United States Patent [19]

Bayne et al.

[11] Patent Number: 4,762,133
[45] Date of Patent: Aug. 9, 1988

[54] CERVICAL CYTOLOGY DEVICE

[75] Inventors: Irman D. Bayne, Littleton; Edwin L. Adair, Denver, both of Colo.

[73] Assignee: Medical Dynamics, Inc., Englewood, Colo.

[21] Appl. No.: 60,917

[22] Filed: Jun. 12, 1987

Related U.S. Application Data

[62] Continuation-in-part of Ser. No. 28,458, Mar. 20, 1987, Pat. No. 4,754,764.

[51] Int. Cl.⁴ .............................................. A61B 10/00
[52] U.S. Cl. .................................. 128/756; 128/759; 128/357; 15/164
[58] Field of Search ............... 128/749, 756, 757, 759, 128/357; 15/164, 165, 106

[56] References Cited

U.S. PATENT DOCUMENTS

| | | | |
|---|---|---|---|
| 680,427 | 8/1901 | Carryl | 15/106 |
| 3,626,470 | 12/1971 | Antonides et al. | 128/759 |
| 3,881,464 | 5/1975 | Levene | |
| 4,448,205 | 5/1984 | Stenkvist | 128/757 |

OTHER PUBLICATIONS

Drs. Christine Bergeron, M.D. and Alex Ferenczy, M.D. "Screening Devices for Cervical and Endometrial Ca" published in Contemporary OB-GYN; pp. 55-66.

Primary Examiner—Kyle L. Howell
Assistant Examiner—Randy Citrin
Attorney, Agent, or Firm—Fields, Lewis, Pittenger & Rost

[57] ABSTRACT

A method and device for simultaneously collecting cytology cell samples from the endocervix and exocervix are disclosed. The device includes a handle for manipulating and rotating the device. Adjacent the handle is an intermediate cell collecting surface which is sized and configured to scrape cell samples from the exocervix when it is in contact with the exocervix and the device is rotated. The device also includes a distal cell collecting surface adjacent the intermediate cell collecting surface. The distal section is sized and configured to scrape cytology cell samples from the endocervical canal when it is located within the canal and in contact with the walls thereof and the device is rotated. The distal and intermediate surface are further positioned on the device with respect to each other to enable the endocervical canal and exocervix to be scraped simultaneously as the device is rotated.

10 Claims, 2 Drawing Sheets

CERVICAL CYTOLOGY DEVICE

This application is a continuation-in-part of Ser. No. 28,458, filed Mar. 20, 1987, now U.S. Pat. No. 4,754,764.

TECHNICAL FIELD

The invention relates generally to a method and apparatus for collecting cell specimens for diagnostic purposes and more particularly to a cervical cytology device and method for collecting cytology cell samples from the uterine endocervix and exocervix.

BACKGROUND ART

It is well-known that uterine cervical cancer can be prevented and/or even cured if it is detected early enough, preferably in its precancerous or precursor stages. Accordingly, women are being encouraged to come in for examinations on a regular basis. Improvements in early detection devices and techniques will also, quite obviously, enhance the physician's ability to accurately detect the presence of cancer in its early stages. Accordingly, much effort is being directed to developing such devices.

Drs. Christine Bergeron, M.D. and Alex Ferenczy, M.D. in their article entitled "Screening Devices for Cervical and Endometrial Ca" published in Contemporary OB-GYN (1987), set forth on pages 55-66 an extensive listing of cervical cytologic sampling and screening devices including wooden spatulas and brushes, and also discuss how the devices should be used to effectively detect the presence of cancer and its precursors.

U.S. Pat. No. 3,881,464 to Levene also discloses a device for obtaining endocervical cell and tissue samples. The device comprises a generally frusto conical brush having a coaxial handle projecting from its larger end. The frusto conical brush consists of soft radially projecting bristles of cellulose acetate which are soluble in a liquid that does not cause morphological damage when the bristles and cell samples are immersed in the liquid. While useful in obtaining cell samples from the endocervical canal, the brush's frusto conical shape does not lend itself to collecting cells from the exocervix.

While the aforementioned devices undoubtedly work as intended, there is still a need for devices which are capable of collecting samples containing more cells, particularly from the exocervix area. The aforementioned wooden spatula does not generally collect enough cells from the exocervix to enable one to accurately determine whether any abnormal cells are present. The problem is even worse with women who have an abnormally or unusually shaped exocervix since the spatula's long rigid lobe may not even make contact with the exocervix. Accordingly, a need still exists for a device which is capable of collecting larger cell samples from the uterine exocervix. Such a device would be even more desirable if it also had the capability of collecting cell samples from the endocervical canal. Such a device would make better use of the physician's time and be more palatable to the patient since it would enable the samples to be taken quicker. Such a device would also be more accurate than presently available devices since it would make it possible to collect larger cell samples from the exocervix.

DISCLOSURE OF THE INVENTION

The present invention addresses the aforementioned concerns and needs by providing a cervical cytology device for simultaneously collecting cytology cell samples from the uterine endocervix and exocervix. In its broad form the device includes a handle for manipulating and rotating the device, an intermediate cell collecting surface region adjacent the handle for scraping cytology cells from the exocervix and a distal cell collecting surface adjacent the intermediate cell collecting surface for scraping cytology cells from the endocervical canal. The cell collecting surfaces are sized and configured to be capable of scraping cytology cell samples from their respective cervical areas when they are in contact with their respective regions of the cervix the device is rotated. The distal and intermediate cell collecting surfaces also positioned with respect to each other on the device so as to enable the endocervical canal and exocervix to be scraped simultaneously as the device is rotated.

A first embodiment of the cervical cytology device of the present invention is a brush which includes a rigid yet bendable shaft having less than three bends which define four sections of the brush. The first bend joins an outwardly projecting or distal cell collecting surface and an intermediate cell collecting surface of the brush. The bend is provided such that the cell collecting surfaces define less than a 90° included angle between their respective shafts. The second bend on the brush's shaft adjoins the intermediate cell collecting surface and an offset intermediate section, and the bend is such that the intermediate sections define approximately a 10° included angle. The third bend joins the intermediate offset section and an outwardly projecting handle section of the brush. This third bend is such that the offset and handle sections define at least a 90° included angle. The bends are also provided so that the distal and handle sections of the brush are axially aligned. In addition, the distal cell collecting surface of the brush is sized and configured to collect cytology cell samples from the endocervical canal when the brush is rotated and the distal cell collecting surface is located within the canal and in contact with the wall thereof. The intermediate cell collecting surface is also sized and configured to collect cytology cell samples from the surface of the exocervix as the distal cell collecting surface is rotated to collect cytology cell samples from the endocervical canal. Accordingly, cell samples from the endocervical and exocervical surface can be collected simultaneously.

The angles described above between the different sections of the brush can be altered at will by the physicians by bending the shaft of the brush. The physician, in effect, can mold the brush to "customize" a "fit" for each individual patient.

In a second embodiment, a distal bristled region is attached to the distal end of a handle and extends axially therefrom. An intermediate bristled region is attached to a disc which surrounds and extends at right angles from a hollow shaft which telescopicly and fixedly engages the distal bristled region shaft and extends substantially the length thereof. With the two portions assembled, the distal bristled region is inserted in the endocervix with the bristled region of the disc against the exocervix. The entire device is rotated so as to collect cells on the respective bristled portions. The portions are then separated from each other whereupon the cells collected on the distal bristled portion from the endocervix can be applied to a first slide and cells collected on the intermediate bristled portion of the disc from the exocervix can be placed on a second slide.

In a third embodiment, a distal bristled portion is provided which is attached to a handle, which is substantially identical to that of the previous embodiment. However, the intermediate bristled portion is provided on a second identical handle and extends at an angle to the distal brush. The two handles are attached to each other along their contiguous surfaces by a fracturable adhesive or weld. When in the assembled welded condition, the brushes are used as described with respect to the previous embodiment. After the cells have been collected, the handles are broken apart along the fracturable weld and the cell samples placed on separate slides for viewing.

The present invention also provides a method of collecting cytology cell samples from the endocervix and exocervix simultaneously. The method includes providing a rotatable cervical cytology device having a first cell collecting surface which is sized and configured to collect cells from the exocervix and a second cell collecting surface which is sized and configured to collect cells from the endocervical canal where the device is rotated. The method further includes inserting the second cell collecting surface into the endocervical canal until the first cell collecting surface is positioned against the surface of the exocervix. The device is then rotated so that cytology cell samples are scraped from the respective surfaces of the exocervix and endocervix simultaneously. As such, the cell samples will collect on the respective first and second cell collecting surface of the device. The device is then withdrawn from the patient. The samples are then removed from the device and examined to determine whether any abnormal cancerous, precancerous or virally diseased cells are present.

Additional advantages of this invention will become apparent from the detailed description which follows, taken in conjunction with the accompanying drawings.

BEST MODE FOR CARRYING OUT THE INVENTION

Figure 1:
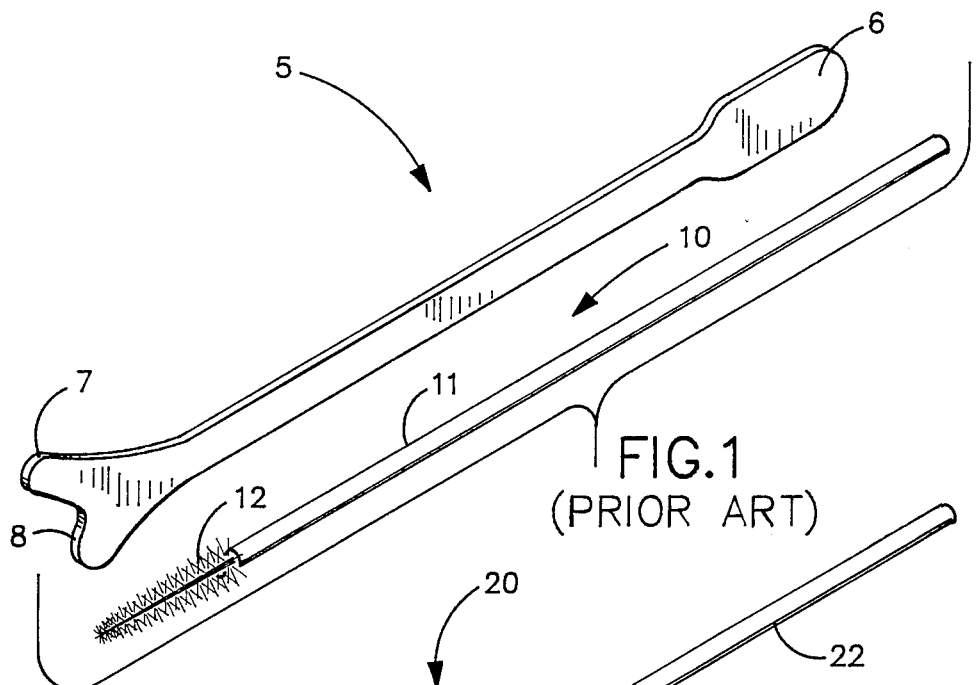
FIG. 1 is a perspective view of a conventional prior art wooden spatula and an endocervical brush which are used by physicians to scrape cytology cell samples from different areas of a uterus.

FIG. 1 illustrates a conventional wooden spatula 5. Drs. Bergeron and Ferenczy describe spatula 5 on page 56 of their above-mentioned article as being a tool for sampling the squamocolumnar junction, the exocervix and to a lesser degree the endocervix. As seen in FIG. 1, one end of spatula 5 is provided with a handle portion 6 for manipulating the spatula. At its other end, spatula 5 is provided with a long lobe 7 and a short lobe 8. In order to collect cervical cell samples for determining whether any abnormal cells are present, spatula 5 is held by handle 6 and inserted into the vagina until the spatula's short lobe 8 is positioned within the patient's endocervical canal entrance and the spatula's long lobe 7 is positioned against the exocervix. Long lobe 7 is then rotated about the exocervix with the short lobe essentially pivoting in the endocervix canal entrance. As such, the long lobe scrapes and collects cells from the surface of the exocervix. The spatula is then withdrawn from the patient and the cells having been collected on the spatula are then removed therefrom and prepared for examination.

Since the spatula's short lobe 8 merely pivots about the endocervical canal entrance, it scrapes and thus collects very few cells from the endocervix. Accordingly, many physicians use other devices to collect endocervical cell samples. FIG. 1 also illustrates an endocervical brush 10 which is one of the more commonly used devices for endocervical sampling. One such brush is sold by International Cytobrush, Inc. under the trademark "Cytobrush". Brush 10 has a thin cylindrical stem-like handle 11 which is about 7½" long. One end of handle 11 is provided with a generally cylindrical brush portion 12 which is generally about ¾" long and about ¼" in diameter. Drs. Bergeron and Ferenczy point out on page 60 of their article that endocervical samples are taken by inserting the brush into the endocervical canal and then slowing rotating it one-half to one full turn. The brush is then removed from the endocervical canal and a pap smear is prepared by rolling and twisting the brush on a glass slide.

Figure 2:
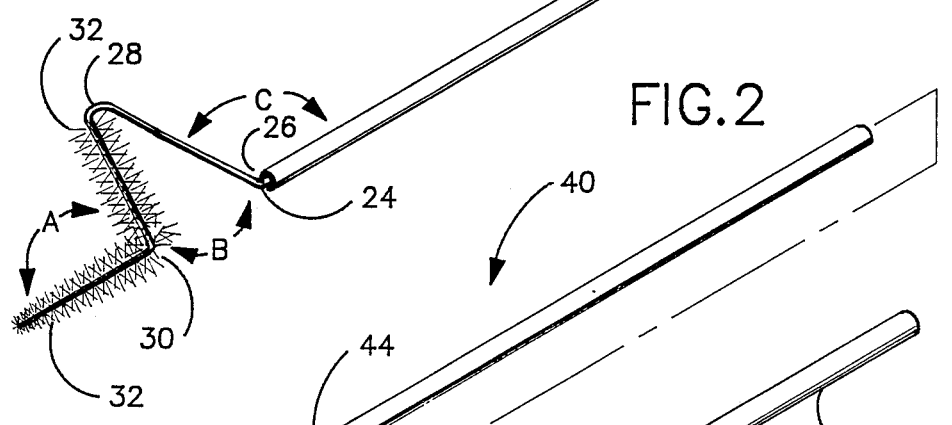
FIG. 2 is a perspective view of a preferred embodiment of the present invention for scraping cytology cell samples from the endocervix and exocervix simultaneously.

FIG. 2 illustrates a first embodiment of a brush 20 of the present invention which is used for collecting cytology cell samples from the uterine endocervix and exocervix simultaneously. Brush 20 includes a handle 22 preferably made from a suitable material, such as, plastic, which is mounted on a shaft 24. It can also be seen that shaft 24 is bent in three places which are identified as bends 26, 28 and 30. Brush 20 is provided with a plurality of radially projecting bristles 32 which extend from bend 28 to the distal end of the brush. The bristles extending between bend 30 and 28 define a generally cylindrically shaped cell collecting surface which is referred herein as the intermediate bristled section of brush 20. It can also be seen that bristles 32 gradually taper from bend 30 to the brush's distal end and, as such, define a generally conical cell collecting surface which is referred to herein as the distal bristled section of the brush. The nonbristled area of shaft 24 between bends 28 and 26 is referred to herein as the intermediate offset section of the brush. The diameter of the intermediate bristled section (i.e. its brush portion) is preferably about ¼". The diameter of the distal bristled section preferably tapers from about ¼" at bend 30 to approximately ⅛" at the brush's distal end.

Bristles 32 are secured to shaft 24 in the conventional helically wound manner (not shown). Accordingly, those skilled in the relevant art will recognize that shaft 24 comprises a pair of strands twisted together. The bristles are tightly secured to the shaft by being interposed between the twisted strands of the shaft.

While the cell collecting surfaces are bristled in the illustrated embodiment it should be understood that they could be made in accordance with the present invention from material which is suitable for collecting or scraping cells from the respective cervical surfaces.

Such materials include closed cell foam materials such as urethane and polyurethane. Other possible materials include sponge-like materials and cotton-like materials such as a cotton swab.

Returning to FIG. 2, bend 30 defines an included angle A between the distal and intermediate bristled sections which is less than 90°, preferably about 85°. Bend 26 between the nonbristled intermediate offset section and the handle section of brush 20 also preferably defines an included angle C of about 100°. Included angle B defined by bend 28 between the intermediate sections is preferably 10° or greater. In addition, the portions of shaft 24 extending through the distal bristled section and the handle section are preferably axially aligned. Further, the height of the offset portions is preferably ¾" as measured from bend 28 to an imaginary line extending between the angled axis of the handle and distal shaft. A brush manufactured as described will conform to the shape of most womens uterine cervixes. However, shaft 24 may be bent to conform to an irregularly shaped cervix. The angle of the bends may also be altered by the physician to custom fit each patient, as required.

In using brush 20 of the present invention, the patient's vaginal cavity is first opened wide, preferably with a vaginal speculum. This permits brush 20 to be easily inserted into the vaginal cavity. The attending physician can also look into the vaginal cavity to see whether the exocervix of the patient is unusually shaped, and if so the physician can bend the brush so that it conforms to the irregularly shaped exocervix. The physician then inserts the brush into the patient's vaginal cavity until the distal bristled end of the brush is inserted within the endocervical canal and the intermediate bristled section of the brush is in contact with the exocervix. The intermediate bristled section should be in contact with the exocervix along its entire length (i.e. from bend 30 to bend 28). If it is not, it should be bent as previously described until it makes such contact. The physician then rotates the brush by rotating the brush handle with his hand so that the bristles of the intermediate bristled section scrape cell samples from the exocervix. As this occurs, cell samples will also be scraped from the endocervical canal walls by the distal bristled section of the brush which will be rotating within the endocervical canal as the brush rotates. After a suitable sample of cells is collected from the endocervix and exocervix, generally after one or two rotations of the brush, the brush is withdrawn from the vaginal cavity. The cell samples on the bristles of the respective brush portions are then removed from the bristles. Since the endocervical and exocervical samples are preferably analyzed separately, the endocervical cells on the distal bristled portion of the brush are removed by smearing them along the length of a first glass side which preferably is done by slowly rotating the distal end of the brush on the slide. The exocervical cells on the intermediate bristled portion of the brush are removed therefrom similarly by smearing them along the length of a second glass slide. The cells of both slides are then placed in a chemical fixative to preserve the cells until they are examined by a pathologist. The pathologist prepares the cells for examination generally by staining them with a Papanicoloff stain. The cells are then examined by the pathologist under a microscope to determine if any abnormal cancerous, precancerous or virally diseased cells are present.

A brush similar to that described in FIG. 2 was tested and found to collect exceedingly good samples, particularly exocervical samples. In fact, the exocervical samples contained on average approximately five times as many cells as those collected by the conventional wooden spatula. These large samples will enhance the physician's ability to more accurately detect the presence of abnormal cancerous and precancerous cells. The samples have also been large enough to enable physicians to detect the presence of virally diseased cells such as herpes.

Figure 3:
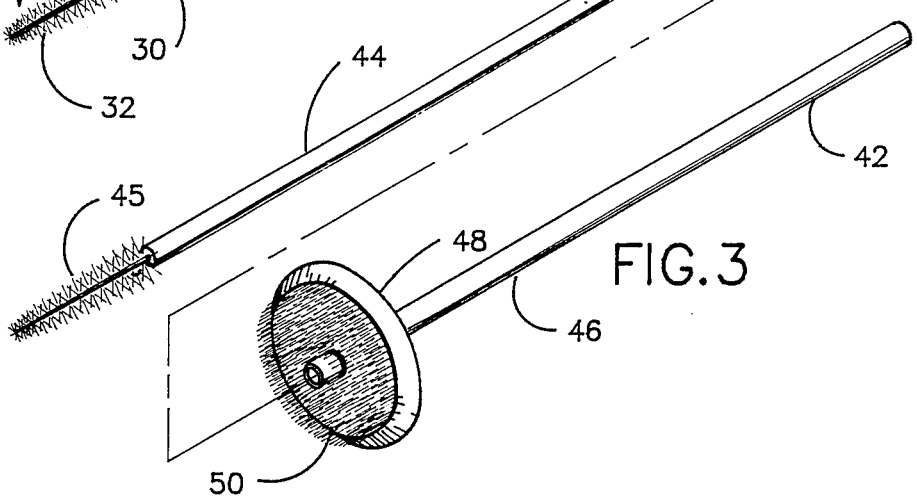
FIG. 3 is an exploded perspective view of another embodiment of the present invention for scraping cytology cell samples from the endocervix and exocervix simultaneously.

FIG. 3 illustrates an alternative brush 40 of the present invention for collecting cell samples from the exocervix and endocervix simultaneously. Brush 40 is provided with two cell collection surfaces, an exocervical brush portion 42 and an endocervical brush portion 44 having bristles 45 at the distal end. While bristled, it should again be understood that other materials suitable for collecting cells could also be used such as urethane or polyurethane.

Endocervical brush portion 44 is similar to the endocervical brush described in FIG. 1, i.e., brush 10. Exocervical brush portion 42 is provided with a hollow shaft 46 which is sized and configured to telescope over the shaft of the endocervical brush portion 44 and fixedly or frictionally engage therewith (i.e., by interference fit) to enable the shafts to rotate together when rotated by an attending physician. Fixed engagement could also be provided by making shallow shaft 46 out of a flexible material which would enable it to compress and frictionally engage the surface of shaft 44 when grabbed by a physician. Interlocking ribs on shafts 44 and 46 could also be employed to provide fixed engagement between the shafts.

Returning to FIG. 3, it can be seen that exocervical brush portion 42 is provided with a disc 48 which is axially disposed on hollow shaft 46 at one end thereof. Disc 48 is provided with bristles 50 on one side and is preferably about 1½" in diameter. Bristles 50 form a generally planar brushing surface. In addition, bristles 50 are long enough (preferably ⅜" long), to enable the brushing surface to conform to the surface of the exocervix, even an irregularly shaped exocervix.

Use of brush 40 is similar to that of brush 20 previously described. The attending physician (after having opened the patient's vaginal cavity with a vaginal speculum) inserts the brush into the vaginal cavity until the endocervical brush portion is located within the endocervical canal and the brushing surface of disc 48 is positioned against the patient's exocervix. The brush is then rotated one or two times to scrape cell samples from the respective endocervix and exocervix. The brush is then withdrawn from the vaginal cavity and the two brush portions, (i.e., exocervical brush portion 42 and endocervical brush portion 44) are separated. Cell samples on the exocervical brush portion are preferably smeared onto one slide and the cell samples from the exocervical brush portion are preferably smeared on another slide. The slides are then prepared and examined to determine if any abnormalities exist.

Figure 4:
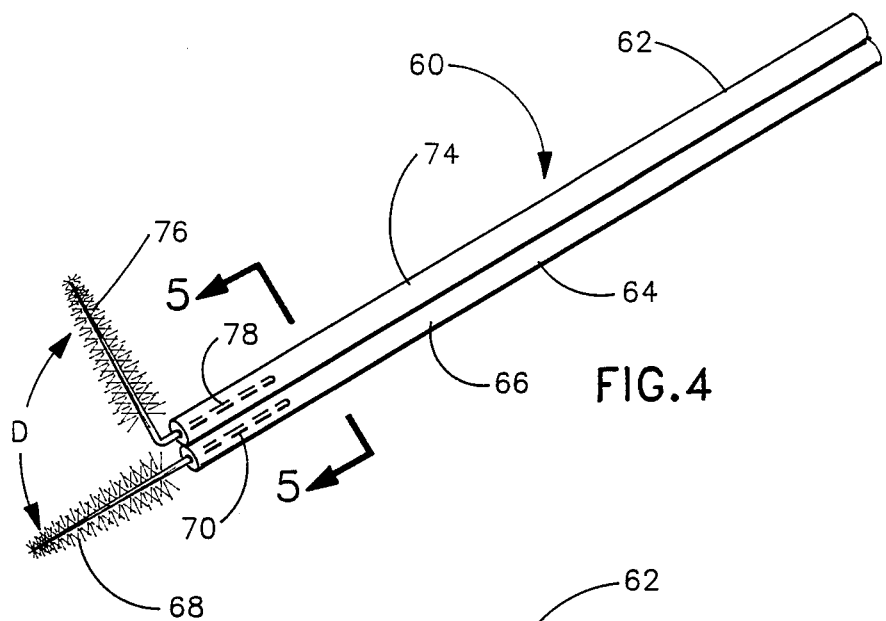
FIG. 4 is a perspective view of a preferred embodiment of the invention having separable handle portions.
Figure 5:
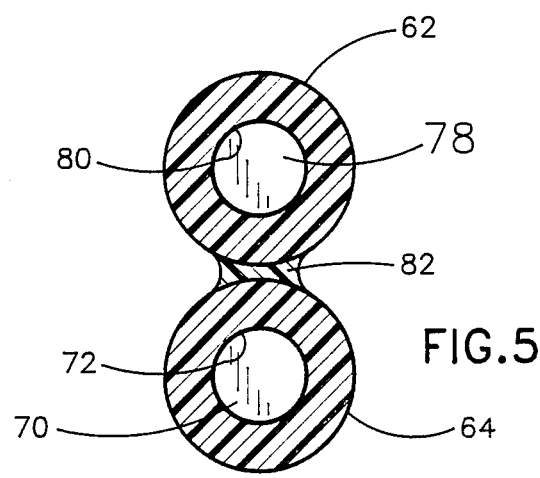
FIG. 5 is an enlarged vertical section, taken along line 5—5 of FIG. 4.
Figure 6:
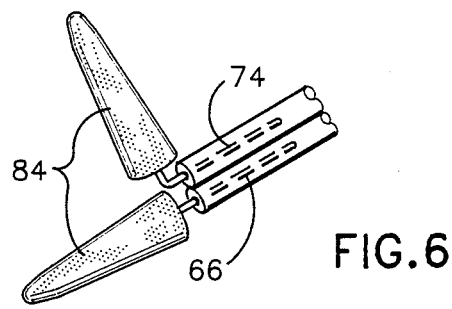
FIG. 6 is a fragmentary perspective view of an alternative device wherein the collecting surfaces are sponge-like closed cell foam or cotton swab material.

A third embodiment in the form of brush 60 is illustrated in FIGS. 4 and 5. Brush 60 has two cell collection surfaces, an exocervical brush portion 62 and endocervical brush portion 64, the later having a handle 66, in the form of a rod, with bristles 68 at the distal end. Although it is illustrated as being bristled, it should be understood that other materials 84 suitable for collecting cells could also be used, such as a cotton swab or a sponge-like material such as urethane or polyurethane after foam as shown in FIG. 6. Conveniently, the brush includes a central wire 70 which extends into a tubular passageway 72 in handle 66. The wire size may be configured to frictionally fit in the passageway or may be secured by a suitable adhesive (not shown).

The exocervical brush portion 62 includes a handle 74 in the form of a rod. An exocervical brush 76 has a central wire 78 which extends into a longitudinal passageway 80 of handle 74. This wire is either sized to frictionally fit in passageway 80 or is attached therein by a suitable adhesive (not shown). Conveniently, wire 78 is bent at an angle so that endocervical brush 68 and exocervical brush 78 have an included angle D between them. This angle, is conveniently approximately 85 degrees. The brush is used in the same manner as the previous embodiment wherein brush 68 is inserted in the endocervix with the brush 76 contacting the exocervix. The brush 60 is rotated along the longitudinal axis of handle 66 so as to collect endocervix cells on brush 68 and exocervix cells on brush 76. The handle 66 and 74 are attached by a weld or adhesive area 82, shown in FIG. 5 which is fracturable. Thus, after the cell samples are collected, the two handles 66 and 74 can be broken apart along the weld 82 and cells on the respective brushes apply to different slides for viewing.

From the foregoing, the advantages of this invention are readily apparent. A cytology brush has been provided which in the various embodiments includes separate cell collecting surfaces, one for collecting the cells from the endocervix and one for collecting cells from the exocervix. After collection, these cell samples can be placed on separate slides for viewing to determine if the patient has any abnormal cell growth.

The invention has been described in detail with particular reference to several embodiments thereof, but it will be understood that variations and modifications can be effected within the spirit and scope of the invention.

We claim:

1. A cervical cytology device for simultaneously collecting cytology cell samples from the endocervix and exocervix, said device comprising:
   handle means for manipulating and rotating said device, said handle means including a pair of parallel rods having surfaces positioned in contiguous relationship, each rod having a distal end and a proximal end;
   fracturable means joining said rods so that they can be separated after use;
   a distal cell collecting surface sized and configured to scrape cytology cell samples from the endocervix, said distal surface being attached to and extending axially from said distal end of one of said rods; and
   an intermediate cell collecting surface sized and configured to scrape cytology cell samples from said exocervix, said intermediate surface being attached to said distal end of said other rod so that said intermediate cell collecting surface extends at an angle from said other rod, said distal cell collecting surface and said intermediate cell collecting surface cooperating, respectfully, to simultaneously scrape cytology cell samples from the endocervix and exocervix, respectfully, when said handle means is rotated and said distal and intermediate cell collecting surfaces are in contact, respectfully, with the endocervix and exocervix.

2. A device, as claimed in claim 1, wherein:
each of said intermediate and said distal cell collecting surfaces includes a shaft provided with a plurality of bristles attached to and projecting radially from said shaft, said bristles of each surface forming a generally cylindrical or conical brush portion.

3. A device, as claimed in claim 2, wherein:
each of said rods is tubular;
said shaft of said distal surface is fixed in said distal end of one of said rods; and
said shaft of said intermediate surface is fixed in said distal end of said other rod; said shaft of said intermediate surface being bent at an angle beyond said distal end of said other rod so that said distal surface and said intermediate surface are at an angle with respect to each other.

4. A device as claimed in claim 3 wherein:
the included angle between said shafts of said distal surface and said intermediate surface is approximately 85°.

5. A device as claimed in claim 1, wherein:
at least one of said cell collecting surfaces includes closed cell foam for collecting cytology cell samples.

6. A device as claimed in claim 5, wherein:
said closed cell foam is selected from the group consisting of urethane or polyurethane.

7. A device as claimed in claim 1, wherein:
at least one of said cell collecting surfaces includes sponge-like material for collecting cytology cell samples.

8. A device as claimed in claim 1, wherein:
at least one of said cell collecting surfaces includes a cotton swab or cotton-like material for collecting cytology cell samples.

9. A device as claimed in claim 1, wherein:
said brush is rigid yet bendable so that said brush is capable of being bent to conform to the shape of a particular exocervix and endocervix to be scraped, said rigidity being such that said brush retains its shape until it is bent again.

10. A device as claimed in claim 1, wherein said fracturable mean is:
a fusion of the rods along said contiguous surfaces.

* * * * *